(12) United States Patent
Naito (10) Patent No.: US 11,583,801 B2
(45) Date of Patent: Feb. 21, 2023

(54) GAS TREATMENT DEVICE AND GAS TREATMENT METHOD

(71) Applicant: Ushio Denki Kabushiki Kaisha, Tokyo (JP)

(72) Inventor: Keisuke Naito, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 17/605,791

(22) PCT Filed: May 8, 2020

(86) PCT No.: PCT/JP2020/018594
§ 371 (c)(1),
(2) Date: Oct. 22, 2021

(87) PCT Pub. No.: WO2020/235349
PCT Pub. Date: Nov. 26, 2020

(65) Prior Publication Data
US 2022/0212143 A1     Jul. 7, 2022

(30) Foreign Application Priority Data

May 21, 2019 (JP) .............................. JP2019-095025

(51) Int. Cl.
*C01B 13/10* (2006.01)
*B01J 23/34* (2006.01)
(Continued)

(52) U.S. Cl.
CPC ....... *B01D 53/8675* (2013.01); *B01D 53/346* (2013.01); *B01D 53/44* (2013.01);
(Continued)

(58) Field of Classification Search
CPC . A61L 9/00; A61L 9/015; A61L 9/032; A61L 9/20; B01D 2257/708;
(Continued)

(56) References Cited

U.S. PATENT DOCUMENTS 5,221,520 A * 6/1993 Cornwell .................. A61L 9/16
422/4
2005/0129591 A1* 6/2005 Wei ......................... B01J 19/123
422/186
(Continued)

FOREIGN PATENT DOCUMENTS

CN    107 314 456 A * 11/2017 ................ F24F 8/22
GB    2 487 544 A * 8/2012 ............... A61L 9/20
(Continued)

OTHER PUBLICATIONS

Supplementary European Search Report for PCT/JP2020/018594, dated May 9, 2020, Attaching a corresponding Taiwanese Application Publication.

*Primary Examiner* — Timothy C Vanoy
(74) *Attorney, Agent, or Firm* — Kenichiro Yoshida (57) ABSTRACT

A gas treatment device that treats a gas to be treated, including oxygen, introduced at a gas inlet and that exhausts a treated gas at a gas outlet, the gas treatment device includes:
  a gas channel that communicates the gas inlet with the gas outlet;
  a blower that allows the gas to be treated to flow from the gas inlet to the gas outlet;
  an ultraviolet light source that is disposed in the gas channel and radiates ultraviolet light having a wavelength of 230 nm or less;
  a filter that is disposed at a side at which the gas outlet is located from the ultraviolet light source in the gas channel, and that adsorbs at least ozone; and
(Continued)

a control unit that controls the blower to operate, wherein the control unit controls the blower to start a blowing operation after the ultraviolet light source starts radiating the ultraviolet light.

18 Claims, 5 Drawing Sheets (51) Int. Cl.
*B01D 53/34* (2006.01)
*B01D 53/44* (2006.01)
*B01D 53/76* (2006.01)
*B01D 53/86* (2006.01)

(52) U.S. Cl.
CPC .............. *B01D 53/76* (2013.01); *B01J 23/34* (2013.01); *C01B 13/10* (2013.01); *B01D 2255/2073* (2013.01); *B01D 2255/9155* (2013.01); *B01D 2257/106* (2013.01); *B01D 2257/708* (2013.01)

(58) Field of Classification Search
CPC ...... B01D 2257/106; B01D 2255/9155; B01D 2255/2073; B01D 53/8675; B01D 53/346; B01D 53/44; B01D 53/76; C01B 13/10; B01J 23/34; G05B 1/00; G05B 6/00; G05B 13/00; G05B 15/00
See application file for complete search history.

(56) References Cited

U.S. PATENT DOCUMENTS

| | | | |
|---|---|---|---|
| 2005/0186108 A1* | 8/2005 | Fields | A61L 2/202 422/123 |
| 2007/0119699 A1* | 5/2007 | Chambers | C01B 13/02 204/176 |
| 2018/0264157 A1* | 9/2018 | Benedek | A61L 9/20 |
| 2021/0170063 A1* | 6/2021 | Benedek | B01D 53/007 |

FOREIGN PATENT DOCUMENTS

| | | | | |
|---|---|---|---|---|
| GB | 2 598 617 A | * | 3/2022 | .............. F24F 13/20 |
| JP | H6-238123 A | | 8/1994 | |
| JP | H7-299128 A | | 11/1995 | |
| JP | H8-131880 A | | 5/1996 | |
| JP | H11-278809 A | | 10/1999 | |
| JP | 2006-296980 A | | 11/2006 | |
| JP | 2008-96039 A | | 4/2008 | |
| JP | 2011-56191 A | | 3/2011 | |
| JP | 2017171540 A | | 9/2017 | |
| KR | 2017 0 061 928 | * | 6/2017 | ............. A61L 9/205 |
| WO | WO 97 34 682 A1 | * | 9/1997 | ............. B01D 53/00 |

* cited by examiner

GAS TREATMENT DEVICE AND GAS TREATMENT METHOD

TECHNICAL FIELD

The present invention relates to gas treatment devices and gas treatment methods, and particularly relates to a gas treatment device and a gas treatment method to treat a gas including volatile organic compounds (VOC).

BACKGROUND ART

There have been concerns about gases that could affect the global environment and human bodies, and certain regulations have been established for exhaust gases from automobiles, factories, etc. Also, the emission regulations of VOC have been established in even indoor places where specific chemicals may be used, such as laboratory facilities and medical sites.

In recent years, there has been developing equipment for decomposing and treating VOC to comply with VOC emission regulations has been developed; in particular, a treatment device using ultraviolet light has been developed as one of its equipment. The Patent Document 1 below, for example, describes a gas treatment device that generates ozone by irradiating oxygen contained in the gas to be treated with ultraviolet rays having a specified wavelength band, and reacts VOC with the ozone for the treatment.

CITATION LIST

Patent Document

Patent Document 1: JP-A-2006-296980

SUMMARY OF INVENTION

Technical Problem

Ozone plays an important role in the treatment of VOC and other substances; however, it has an odor and is known to adversely affect the human body. Hence, most of the gas treatment device using ozone to treat VOC, similar to the gas treatment device in Patent Document 1 described above, is equipped with an ozone filter to adsorb or decompose ozone to prevent ozone from discharging at a gas outlet at which the treated gas is exhausted.

The ozone filter, however, has difficulty in selectively adsorbing only ozone; it also adsorbs VOC that has not been treated. This phenomenon is not a characteristic of ozone filters; instead, it is a property of VOC that tends to adhere to and accumulates on the surface of material when contacting with it.

When VOC adheres to and accumulates on the surface of the ozone filter, the ozone filter has reduced surface areas that can adsorb ozone, resulting in a decrease in adsorption power. Part of the VOC attached to the surface of the ozone filter is removed from the surface of the ozone filter by the airflow generated in the gas channel, and is exhausted with the treated gas at the gas outlet.

In other words, if the gas treatment device as described above in Patent Document 1 is used without some kind of control, untreated VOC will be deposited on the surface of the ozone filter. Then, the VOC deposited on the surface of the ozone filter is gradually separated from the ozone filter by the airflow generated in the gas channel, and is gradually exhausted at the gas outlet. Thus, part of the VOC is eventually exhausted outside the gas treatment device.

In response to the above problems, it is an object of the present invention to provide a gas treatment device and a gas treatment method that suppress the amount of VOC attached to a filter that adsorbs ozone, and maintain low concentration of VOC exhausted for a long period.

Solution to Problem

A gas treatment device of the present invention that treats a gas to be treated, including oxygen, introduced at a gas inlet and that exhausts a treated gas at a gas outlet disposed at a location different from that of the gas inlet, the gas treatment device includes:

a gas channel that communicates the gas inlet with the gas outlet;

a blower that allows the gas to be treated to flow from the gas inlet to the gas outlet;

an ultraviolet light source that is disposed in the gas channel and radiates ultraviolet light having a wavelength of 230 nm or less;

a filter that is disposed at a side at which the gas outlet is located from the ultraviolet light source in the gas channel, and that adsorbs at least ozone; and a control unit that controls the blower to operate, wherein the control unit controls the blower to start a blowing operation after the ultraviolet light source starts radiating the ultraviolet light.

The gas treatment device of the present invention is used at, for example, part of draft chambers where work are performed using chemicals such as formalin, and exhaust ducts in laboratories. The gas treatment device of the present invention intakes a gas to be treated from the gas inlet, and treats the gas to be treated with contacting ozone or radicals that are generated by ultraviolet light radiated from the ultraviolet light source, while allowing the gas to be treated to flow toward the gas outlet.

Ozone is generated, as described above, by irradiating oxygen contained in the gas to be treated with ultraviolet light radiated from the ultraviolet light source. To generate ozone by irradiating oxygen with ultraviolet light, the ultraviolet light source preferably radiates ultraviolet light having a wavelength of 230 nm or less, photon energy of which being capable of generating ozone from oxygen.

The gas to be treated, together with oxygen, are introduced into the gas channel at the gas inlet with the blower and flows around the ultraviolet light source. Then ultraviolet light having a wavelength of 230 nm or less, radiated from the ultraviolet light source is radiated to oxygen contained in the gas to be treated, to form ozone. The gas to be treated reacts with the ozone to be decomposed. Then the gas to be treated flows through a filter and is exhausted at the gas outlet as an exhaust gas. The ozone that has not contributed to the treatment is adsorbed and decomposed at the filter, avoiding ozone with high concentration being exhausted at the gas outlet.

Hence, to treat the gas to be treated that is introduced into the gas channel at the gas inlet, the ultraviolet light source needs to radiate ultraviolet light when the gas to be treated has reached the vicinity of the ultraviolet light source. If the ultraviolet light source does not radiate ultraviolet light when the gas to be treated has reached the ultraviolet light source, no ozone is generated, thus the gas to be treated fails to be treated, simply flowing toward the filter. As a result, VOC contained in the gas to be treated is attached to the filter, or is directly exhausted at the gas outlet.

In the above configuration, the ultraviolet light source has radiated ultraviolet light at a time when the blower starts blowing operation, preventing the gas to be treated introduced at the gas inlet from passing around the ultraviolet light source that has not started radiating ultraviolet light and flowing to the filter.

In addition, since the control unit controls the blower to start the blowing operation after the ultraviolet light source have started radiating ultraviolet light, this configuration eliminates the concern that operators mistakenly start the blowing operation of the blower sooner than the ultraviolet radiation. Moreover, even in the case of starting from the state in which the ultraviolet light source stops lighting and the blower operates the blowing, the control unit waits for a while until the blower stops the blowing operation, and as described above, controls the blower to start the blowing operation after the ultraviolet light source has started radiating ultraviolet light.

To cope with a case in which the gas to be treated flows to the filter before the ultraviolet light source radiates ultraviolet rays, the case including the flow due to natural convection, or the blowing operation that the blower has mistakenly started prior to the ultraviolet light radiation of the ultraviolet light source, a mechanism (e.g., a shielding plate, a shutter, etc.) may be provided to block the gas channel until the ultraviolet light source radiates ultraviolet light. This configuration further suppresses the amount of VOC that fails to have been treated, flows toward the filter and is attached to the filter.

The control unit of the gas treatment device may control the blower to stop the blowing operation after the ultraviolet light source stops radiating the ultraviolet light.

In the case of stopping the gas treatment device, when the blower stops the blowing operation before stopping the radiation of ultraviolet light from the ultraviolet light source, the flow of the gas to be treated in the gas channel stops; however, ozone is continuously generated by ultraviolet light radiated from the ultraviolet light source. The ozone generated by ultraviolet light radiated from the ultraviolet light source reacts with VOC, if any VOC remains around the ultraviolet light source, and dissipates.

However, since the blower stops the blowing operation, the gas to be treated is barely introduced from the gas inlet. The gas flow in the gas channel also stops, thus ozone generated in the gas channel neither react with VOC nor flow toward the filter. In other words, ozone generated in the gas chamber gradually diffuses in the gas channel, posing a risk that part of the ozone eventually leaks outside at the gas outlet.

As described above, ozone has odor and adversely affects to human bodies, thus it is not desirable to exhaust outside the gas treatment device; ozone generated in the gas channel is preferably adsorbed and decomposed with the ozone filter as much as possible.

Hence, the configuration described above enables the state in which the blower continues the blowing operation during the generation of ozone in the gas chamber, by the ultraviolet light radiation from the ultraviolet light source. Therefore ozone generated in the gas channel flows toward the ozone filter, preventing ozone from diffusing toward the gas inlet and leaking outside at the gas inlet.

If the control unit fails to operate the control described above, an operator needs to instruct the ultraviolet light source to stop lighting and also to instruct the blower to stop blowing individually. During this operation, it is possible that the operator mistakenly stops the blowing operation of the blower before stopping lighting the ultraviolet light source. In the above configuration, however, the control unit automatically controls the blower to stop the blowing operation after the ultraviolet light source stops radiating ultraviolet light, preventing the unexpected situation described above from occurring. Moreover, even in the case of stopping from the state in which the ultraviolet light source lights and the blower does not operate the blowing, the control unit waits until the blower stops the blowing operation, and as described above, controls the blower to stop the blowing operation after the ultraviolet light source has stopped radiating ultraviolet light.

The control unit of the gas treatment device may control the lighting of the ultraviolet light source.

The above configuration can set the control sequence from lighting the ultraviolet light source to starting the blowing operation of the blower, and the control sequence from turning off the ultraviolet light source to stopping the blowing operation of the blower.

For example, by controlling the blower to start the blowing operation several hundred milliseconds to several seconds after the lighting of the ultraviolet light, this makes it possible to ensure the sufficient time for the ultraviolet light source to start radiating ultraviolet light after the start of the light emission of the ultraviolet light source. Also, by controlling the blower to stop the blowing operation several seconds to several minutes after turning off the ultraviolet light, this makes it possible to ensure the sufficient time for the ozone remaining in the gas channel after stopping the generation of ozone to flow toward the side of the filter, where the ozone is adsorbed and decomposed.

The above gas treatment device may include an operation instruction unit that is configured to be operational to an operator, wherein the operation instruction unit may transmit a treatment start signal to the control unit when the operator operates the operation instruction unit to perform a start of an operation, and the control unit may perform a first control that lights the ultraviolet light source and a second control that starts the blowing operation of the blower after executing the first control when the control unit receives the treatment start signal transmitted from the operation instruction unit.

In addition, in the gas treatment device described above, the operation instruction unit may transmit a treatment stop signal to the control unit when the operator operates the operation instruction unit to perform a stop of the operation during the lighting of the ultraviolet light source, and the control unit may perform a third control that turns off the ultraviolet light source and a fourth control that stops the blowing operation of the blower after executing the third control when the control unit receives the treatment stop signal transmitted from the operation instruction unit.

In the above configuration, the gas treatment device can start with an appropriate sequence and also stop with an appropriate sequence just by the operation of the operation instruction unit, preventing an operation mistake by an operator.

In the case of stopping the gas treatment device, the radiation of ultraviolet light from the ultraviolet light source and the blowing operation of the blower may be configured to continue for a predetermined time after an operator operates the operation instruction unit and until the ultraviolet light source is turned off. The above configuration can treat the gas to be treated remaining in work spaces or draft chambers.

The ultraviolet light source of the gas treatment device may be an excimer lamp that radiates ultraviolet light having a main emission wavelength of 172 nm.

Some materials contained in the gas to be treated are difficult to be decomposed by ozone. Formaldehyde, for example, is difficult to be decomposed by ozone; instead it is decomposed by hydroxyl radicals generated when ultraviolet light radiates water mainly contained in the gas to be treated.

In the case of using an excimer lamp, which consists of a tube made of synthetic quartz glass filled with a discharge gas containing Xe, as an ultraviolet light source, it can radiate ultraviolet light having a main emission wavelength of 172 nm when a voltage is applied between its electrodes. Ultraviolet light, radiated from the ultraviolet light source, having a main emission wavelength of 172 nm enable generation of both of ozone and hydroxyl radicals.

A gas treatment method of the present invention is a method of treating a gas to be treated, including oxygen, that is introduced at a gas inlet, allowing the gas to be treated to flow through a filter that adsorbs at least ozone, and exhausting a treated gas at a gas outlet disposed at a location different from that of the gas inlet, the method includes:

a step (A) of starting radiation of ultraviolet light from an ultraviolet light source; and a step (B) of starting a blowing operation of a blower to allow the gas to be treated to flow from the gas inlet toward the gas outlet, after executing the step (A).

The above method, as described above, prevents the gas to be treated introduced at the gas inlet by starting the blowing operation of the blower from passing around the ultraviolet light source that has not started radiating ultraviolet light, and from flowing to the filter.

The gas treatment method may include a step (C) of stopping the radiation of the ultraviolet light from the ultraviolet light source and a step (D) of stopping the blowing operation of the blower, the blowing operation allowing the gas to be treated to flow in the gas channel from the gas inlet toward the gas outlet after executing the step (C).

The above method ensures, as described above, that the blower is continuously in a state of the blowing operation during ozone is generated in the gas chamber by the radiation of ultraviolet light radiated from the ultraviolet light source. Hence, ozone generated in the gas channel is made to flow toward the side of the filter, preventing the ozone from leaking out of the gas inlet.

Advantageous Effects of Invention

According to the present invention, achieved are a gas treatment device and a gas treatment method that suppress the amount of VOC attached to a filter that adsorbs ozone and maintain low concentration of VOC exhausted for a long period.

DESCRIPTION OF EMBODIMENTS

Hereinafter, the gas treatment device and the gas treatment method of the present invention will now be described with reference to the drawings. It is noted that each drawing is schematically illustrated; ratios and numbers on the drawings do not match those of the actual device.

Figure 1:
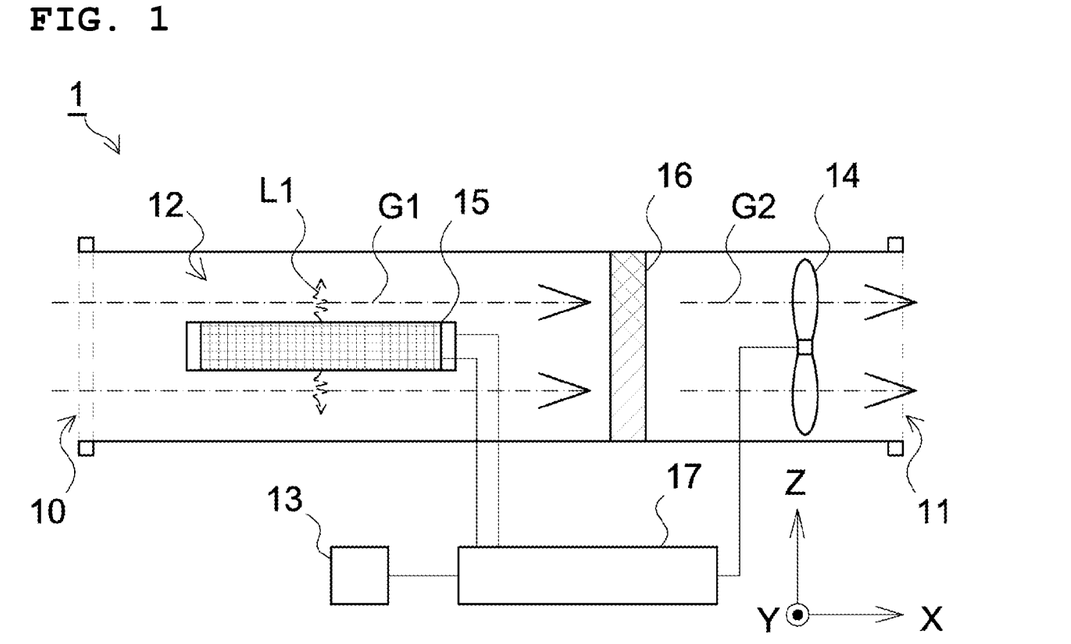
FIG. 1 is a cross-sectional view schematically illustrating an embodiment of a gas treatment device, viewed from the side thereof.

FIG. 1 is a cross-sectional view schematically illustrating an embodiment of a gas treatment device 1, viewed from the side thereof. The gas treatment device 1 is intended to be used in an application in which a gas to be treated G1 containing VOC and oxygen (i.e. air containing VOC) is treated in order to reduce the concentration of the VOC. As described in the FIG. 1, the gas treatment device 1 includes a gas inlet 10 that introduces the gas to be treated G1 from outside, an gas outlet 11 that exhausts an exhaust gas G2 outside, a gas channel 12 configured to communicate the gas inlet 10 with the gas outlet 11, an operation instruction unit 13 that an operator operates to start and stop the treatment with the gas treatment device 1. The operation instruction unit 13 may be configured to, for example, physical elements that are operational to the operator such as a switch and button, or a touch panel.

In the gas channel 12, the gas treatment device 1 includes a blower 14 that allows the gas to be treated G1 to flow from the gas inlet 10 toward the gas outlet 11, an ultraviolet light source 15 that radiates oxygen contained in the gas to be treated G1 with ultraviolet light L1 in order to generate ozone, a filter 16 that adsorb ozone generated with the ultraviolet light source 15 at the side of the gas outlet 11 from the ultraviolet light source 15. In addition, the gas treatment device 1 includes a control unit 17 that receives the treatment start signal from the operation instruction unit 13 and controls the lighting of the ultraviolet light source 15 and the operation of the blower 14.

Hereinafter, as shown in FIG. 1, the direction from the gas inlet 10 toward the gas outlet 11 is denoted as the X direction, and the surface orthogonal to the direction is denoted as the YZ plane.

The gas channel 12 may not be a shape extended in the X direction as shown in FIG. 1; it may be a curved shape or a configuration that changes the direction of flow in the middle of the channel. The blower 14 is, for example, a blower fan. The blower 14 may not be configured to be disposed in the gas channel 12 as long as it has a function that allows the gas to be treated G1 to flow from the side of the gas inlet 10 to the side of the gas outlet 11.

Figure 2:
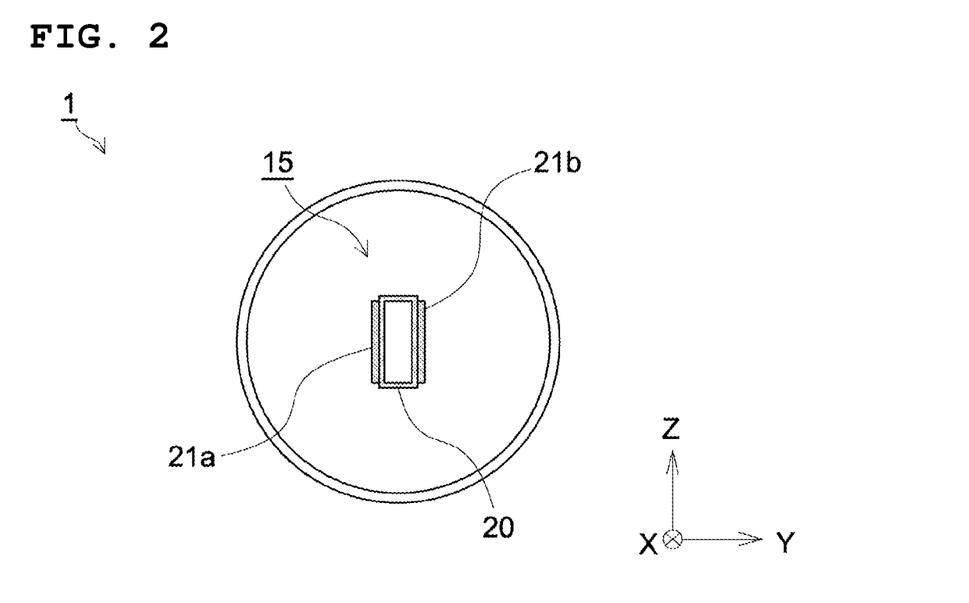
FIG. 2 is a cross-sectional view of the embodiment of the gas treatment device in FIG. 1 cut along the YZ plane at the center portion of an ultraviolet light source.

FIG. 2 is a cross-sectional view of the embodiment of the gas treatment device 1 in FIG. 1 cut along the YZ plane at the center portion of the ultraviolet light source 15. As shown in FIGS. 1 and 2, the ultraviolet light source 15 according to the present embodiment is an excimer lamp consisting of a cylindrical tube body 20 made of synthetic quartz glass and filled with discharge gas containing Xe, and is disposed such that its lamp axis is along the X direction.

As shown in FIGS. 1 and 2, the ultraviolet light source 15 is an excimer lamp having a shape called a flat tube shape, that includes a tube body 20 whose shape is rectangular when viewed from the X direction, and electrodes (21a, 21b) each formed on the side surface of the tube body 20 facing each other. The ultraviolet light source 15 radiates ultraviolet light L1 having a main emission wavelength of 172 nm when a voltage is applied between the electrodes (21a, 21b). A plurality of the ultraviolet light sources 15 may be disposed in the gas channel 12.

A filter 16 is a filter that adsorbs ozone, for example, a catalytic filter, etc., and may have a lattice structure, a honeycomb structure, or a structure in which a chip-shaped adsorbent is laid.

Figure 3:
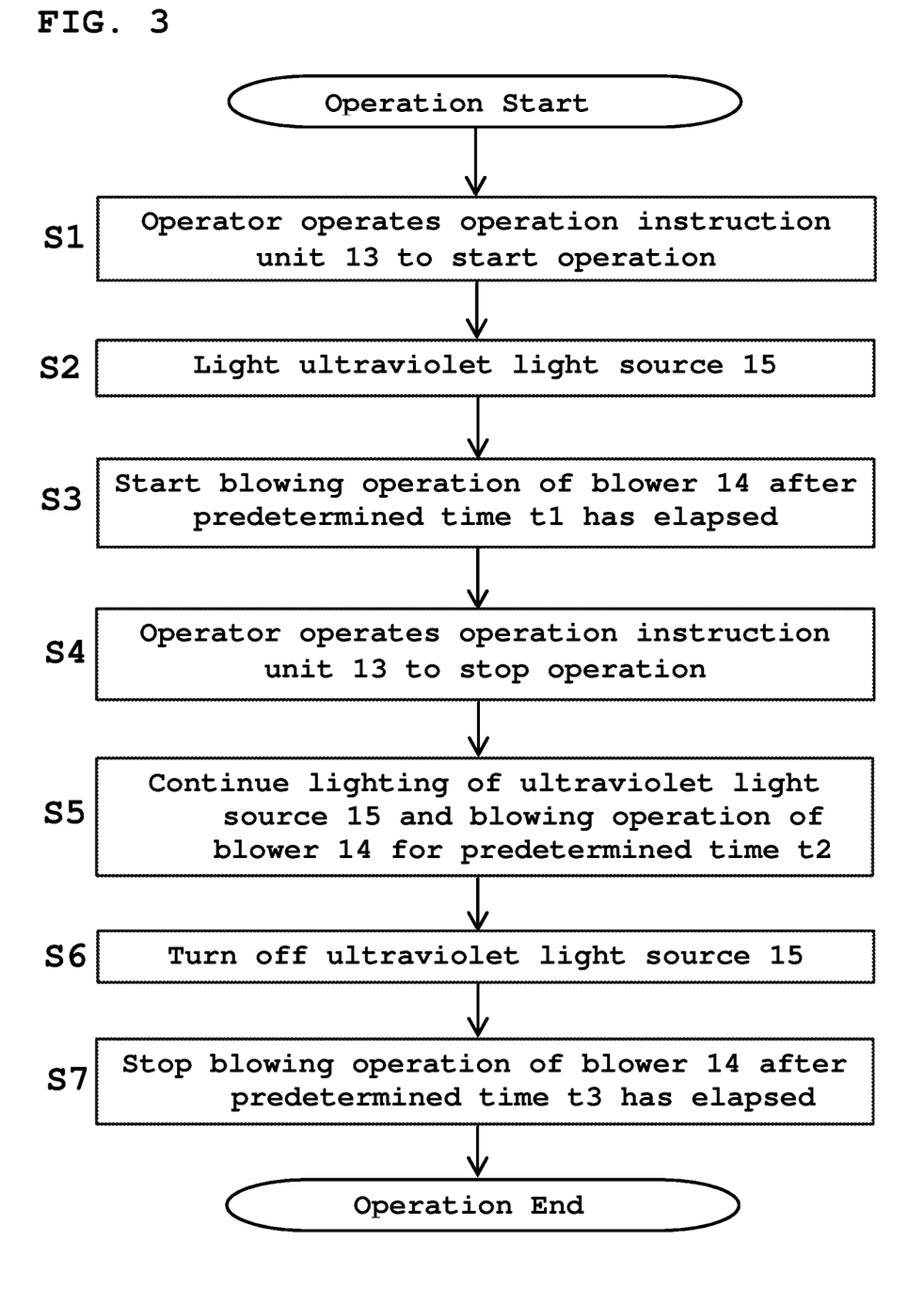
FIG. 3 is a flow chart describing a control sequence of a control unit.
Figure 4:
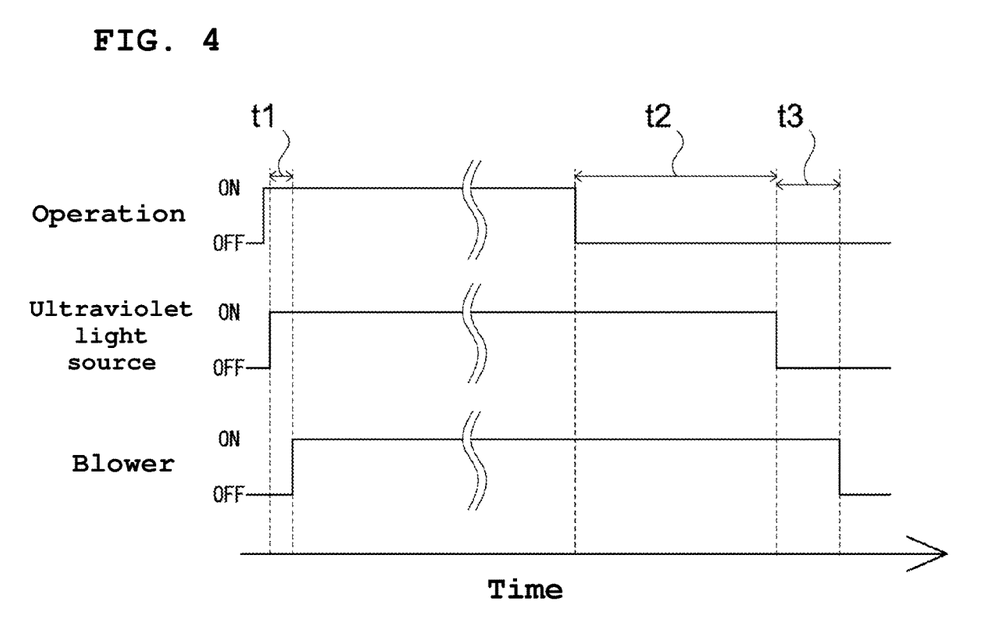
FIG. 4 is a timing chart describing a control of the control unit in time series.

FIG. 3 is a flow chart describing a control sequence of a control unit 17. FIG. 4 is a timing chart describing a control of the control unit 17 in time series. As shown in FIGS. 3 and 4, the operation instruction unit 13 transmits the treatment start signal to the control unit 17 when an operator operates the operation instruction unit 13 to perform a start the operation (S1).

The control unit 17 controls the lighting of the ultraviolet light source 15 (first control, S2) when it receives the treatment start signal transmitted from the operation instruction unit 13, then controls the start of the blowing operation of the blower 14 (second control, S3) when a time t1 necessary for the ultraviolet light source 15 to radiate ultraviolet light L1 has elapsed.

The operator can perform experiments or the like using such as chemical agents after the ultraviolet light source 15 lights and the blower 14 starts the blowing operation. The gas treatment device 1 introduces the gas to be treated G1 containing VOC generated from, for example, chemical agents, at the gas inlet 10, and treats the gas to be treated G1 by contacting ozone and radicals generated by the ultraviolet light L1 radiated from the ultraviolet light source 15 while the gas to be treated G1 flows toward the gas outlet 11. Ozone that has not been used for the treatment is adsorbed and decomposed with a filter 16. In this way, the exhaust gas G2 is exhausted at the gas outlet 11 to the outside of the gas treatment device 1 as a clean air.

The operation instruction unit 13 transmits the treatment stop signal to the control unit 17 when the operator operates the operation instruction unit 13 to perform a stop of the operation to finish work (S4). when the control unit 17 receives the treatment stop signal transmitted from the operation instruction unit 13, the control unit 17 controls the lighting of the ultraviolet light source 15 and the blowing operation of the blower 14 to continue for a predetermined time t2 (S5), and then controls the ultraviolet light source to turn off (third control, S6). The control unit 17 controls the blower 14 to stop the blowing operation (fourth control) when a time t3 necessary for ozone in the gas channel 12 to be sufficiently adsorbed and decomposed with the filter 16 has elapsed (S7), thus terminating the operation.

Each of the time is controlled by, for example, a timer or a sequencer. In the case of the gas treatment device 1 of the present embodiment, the time t1 taken from the control of lighting the ultraviolet light source 15 to the start of the blowing operation of the blower 14 is set to be 1 second. Also, in the present embodiment, the time t2, for which the control unit 17 continues the treatment operation after receiving the treatment stop signal, is set to be 1 hour; the time t3, for which the control unit 17 controls the blower 14 to stop the blowing operation after the control of turning off the ultraviolet light source 15, is set to be 1 minute.

The above configuration prevents the gas to be treated G1 from passing around the unlit ultraviolet light source 15 and flowing toward the filter 16, and from leaking outside at the gas inlet 10. In addition, the operator can start and stop the gas treatment device 1 with an appropriate sequence only by operating the operation instruction unit 13, thus preventing operational mistake or the like.

Since the gas treatment device 1 of the present invention does not allow the gas to be treated G1 to pass around the unlit ultraviolet light source 15 and flow toward the filter 16, thus minimizing the amount of VOC, which is contained in the gas to be treated G1, attached to the filter 16, as well as suppressing the amount of VOC, which is contained in the gas to be treated G1, exhausted at the gas outlet 11, therefore leading to using the filter for a long time.

(Verification)

To verify the effectiveness of the embodiment above, indicated are the results of comparative verification of the amount of VOC exhausted from the gas outlet 11 after starting the gas treatment device 1 in the reverse control sequence of the embodiment described above. This verification was performed using formaldehyde as a VOC that is a substance to be treated contained in the gas to be treated G1.

(Verification Method)

The ultraviolet light source 15 was disposed in the gas channel 12, and the filter 16 was disposed in the gas channel 12 at the side at which the gas outlet is located from the ultraviolet light source 15. Air containing 14 to 22 ppm formaldehyde was used as the gas to be treated G1, and flowed from the gas inlet 10 through the gas channel 12 at a flow rate of 1000 L/min. From the time when the ultraviolet light source 15 was turned on, the concentration of formaldehyde contained in the exhaust gas G2 exhausted at the gas outlet 11 was measured with time.

The gas channel had a length of 5.0 m from the gas inlet 10 to the gas outlet 11. The blower 14 was disposed at 4.5 m from the gas inlet 10, the ultraviolet light source 15 was disposed at 1.0 m from the gas inlet 10, and the filter 16 was disposed at 2.0 m from the gas inlet 10.

The ultraviolet light source 15 was an excimer lamp having a flattened tube structure as shown in FIG. 2. The filter 16 was a catalytic filter having a metal honeycomb structure as base material made of aluminum supported with manganese dioxide as a catalyst.

Example 1

The ultraviolet light source 15 was turned on, and after 1 minute, the blower 14 was started for the blowing operation.

Comparative Example 1

The blower 14 was started for the blowing operation, and after 1 minute, the ultraviolet light source 15 was turned on.

(Result)

Figure 5:
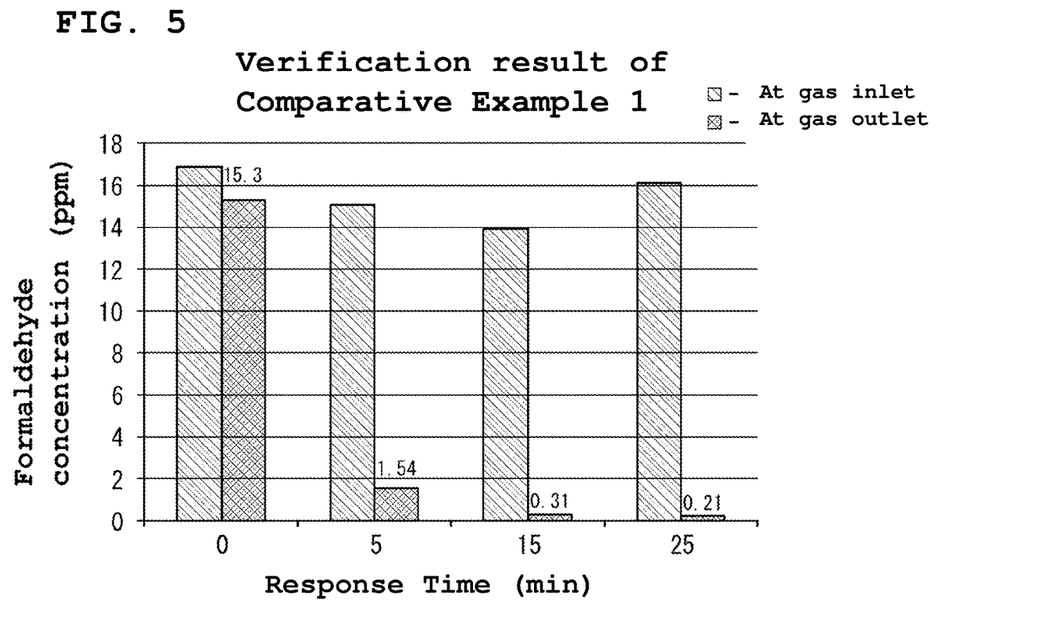
FIG. 5 is a graph indicating a verification result of Example 1.

FIG. 5 is a graph showing the verification result of Comparative Example 1. In Comparative Example 1, the formaldehyde concentration at the gas outlet 11 was 15.3 ppm immediately after the start of the verification, which is a slight reduced value than the formaldehyde concentration at the gas inlet 10. This result is explained by the fact that the ultraviolet light source 15 was not turned on immediately after the start of the verification, thus the gas to be treated G1, which was introduced into the gas channel 12 at the gas inlet 10, was exhausted at the gas outlet 11 almost as it was.

The formaldehyde concentration at the gas outlet 11 was measured at 1.54 ppm after 5 minutes, 0.31 ppm after 15 minutes, and 0.21 ppm after 25 minutes. The concentration of formaldehyde in the exhaust gas G2 exhausted at the gas outlet 11 was not reduced to 0.1 ppm or less even though the gas treatment device 1 was operated for 25 minutes.

Figure 6:
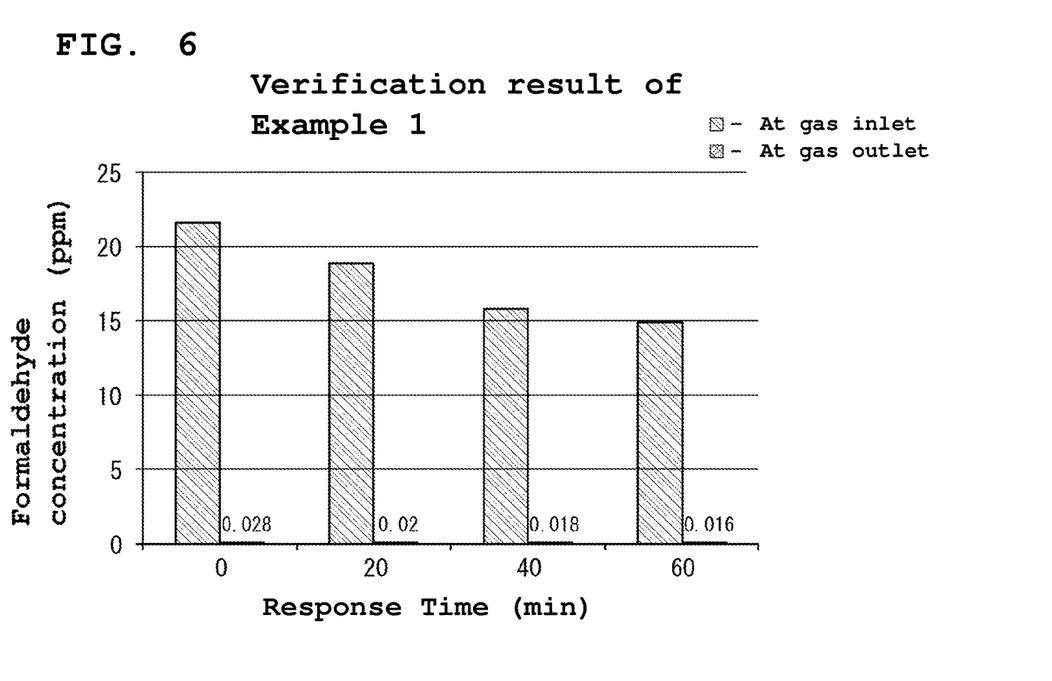
FIG. 6 is a graph indicating a verification result of Comparative Example 1.

FIG. 6 is a graph showing a verification result of Example 1. As shown in the graph in FIG. 6, in Example 1, the formaldehyde concentration at the gas outlet 11 was 0.028 ppm immediately after the start of the verification, thus the concentration of formaldehyde contained in the exhaust gas G2 exhausted at the gas outlet 11 was 0.1 ppm or less immediately after the start of the verification.

The concentration of formaldehyde at the gas outlet 11 was measured at 0.02 ppm after 20 minutes, 0.018 ppm after 40 minutes, and 0.016 ppm after 60 minutes. The concentration of formaldehyde in the exhaust gas G2 exhausted at the gas outlet 11 was not increased even though the gas treatment device 1 was operated for 60 minutes. This result indicates that the gas to be treated G1 introduced into the gas channel 12 at the gas inlet 10 is sequentially decomposed and treated, hence no formaldehyde or the like virtually accumulates in the filter 16 and is gradually discharged at the gas outlet 11 with the blowing operation.

Another Embodiment

Hereinafter, another embodiment is described.

<1> The control unit 17 may control the blower 14 to start the blowing operation when the control unit 17 detects that the ultraviolet light source 15 radiates the ultraviolet light L1 with a sensor detecting the ultraviolet light L1 after the control of lighting the ultraviolet light source 15. Further, the control unit 17 may control the blower 14 to stop the blowing operation when the control unit 17 measures the ozone concentration in the gas channel 12 and detects that the measured value becomes a predetermined concentration or less after the control of turning off the ultraviolet light source 15.

The above configuration enables the blower 14 to start the blowing operation in the state that the ultraviolet light source 15 securely radiates at the start of the operation, and to stop the blowing operation after confirming the ozone concentration in the gas channel 12 is sufficiently low at the stop of the operation.

Figure 7:
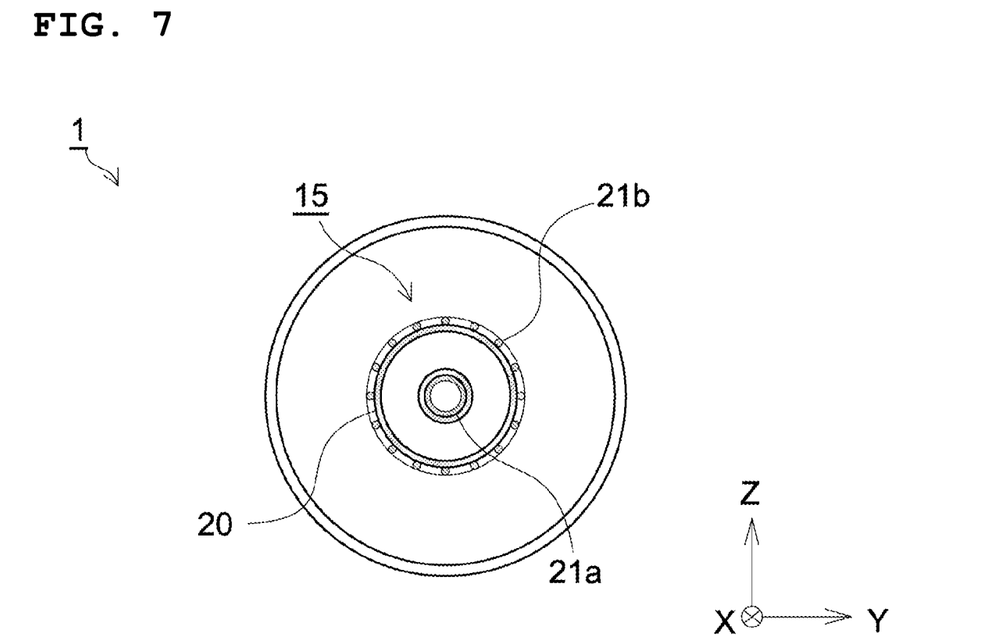
FIG. 7 is a cross-sectional view of another embodiment of the gas treatment device cut along the YZ plane at the center portion of an ultraviolet light source.

<2> FIG. 7 is a cross-sectional view of another embodiment of the gas treatment device 1 cut along the YZ plane at the center portion of an ultraviolet light source 15. As shown in FIG. 7, the excimer lamp used for the ultraviolet light source 15 may be an excimer lamp having a shape called a double tube shape, the lamp having a cylindrical shape when viewed in an extending direction of a tube body 20, and being provided with an electrode 21a on an inner wall surface thereof and an electrode 21b on an outer wall surface thereof.

Figure 8:
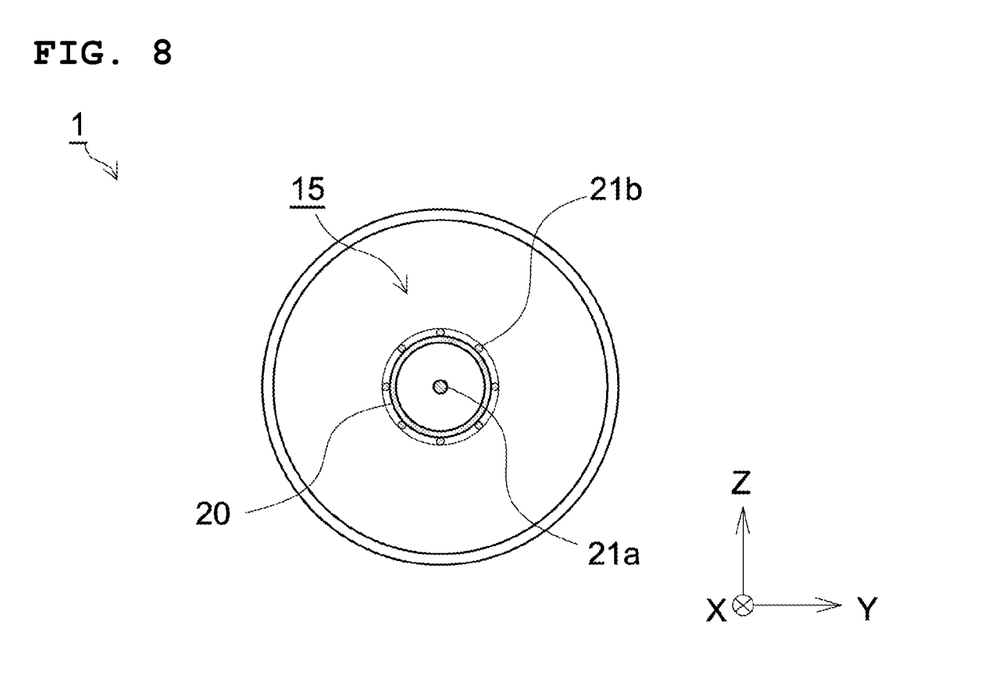
FIG. 8 is a cross-sectional view of still another embodiment of the gas treatment device cut along the YZ plane at the center portion of an ultraviolet light source.

<3> FIG. 8 is a cross-sectional view of still another embodiment of the gas treatment device cut along the YZ plane at the center portion of an ultraviolet light source 15. As shown in FIG. 8, the excimer lamp used for the ultraviolet light source 15 may be an excimer lamp having a shape called a tube shape, the lamp having a cylindrical shape when viewed in an extending direction of a tube body 20, and being provided with an electrode 21a inside the tube body 20 and an electrode 21b on an outer wall surface thereof.

<4> The ultraviolet light source 15 may be a light source other than excimer lamps, such as low-pressure mercury lamps or LEDs, as long as it radiates ultraviolet light L1 having a wavelength of 230 nm or less.

<5> The VOC contained in the gas to be treated G1 are not limited to formaldehyde; Examples include methanol, IPA (isopropyl alcohol), acetone, ethylene oxide, toluene, xylene, ethyl acetate.

<6> The configurations of the gas treatment device 1 described above are merely examples, and the present invention is not limited to each of the configurations described above.

REFERENCE SIGNS LIST 1 gas treatment device
10 gas inlet
11 gas outlet
12 gas channel
13 operation instruction unit
14 blower
15 ultraviolet light source
16 filter
17 control unit
20 tube body
21a, 21b electrode
G1 gas to be treated
G2 exhaust gas
L1 ultraviolet light

The invention claimed is:

1. A gas treatment device that treats a gas to be treated, including oxygen, introduced at a gas inlet and that exhausts a treated gas at a gas outlet disposed at a location different from that of the gas inlet, the gas treatment device comprising:
a gas channel that communicates the gas inlet with the gas outlet;
a blower that allows the gas to be treated to flow from the gas inlet to the gas outlet;
an ultraviolet light source that is disposed in the gas channel and emits ultraviolet light having a wavelength of 230 nm or less;
a filter that is disposed at a side at which the gas outlet is located from the ultraviolet light source in the gas channel, and that adsorbs at least ozone; and
a control unit that controls the blower to operate,
wherein the control unit controls the blower to start a blowing operation after the ultraviolet light source starts radiating the ultraviolet light.

2. The gas treatment device according to claim 1, wherein the control unit controls the blower to stop the blowing operation after the ultraviolet light source stops radiating the ultraviolet light.

3. The gas treatment device according to claim 2, wherein the control unit controls the lighting of the ultraviolet light source.

4. The gas treatment device according to claim 3, further comprising an operation instruction unit that is configured to be operational to an operator,
wherein the operation instruction unit transmits a treatment start signal to the control unit when the operator operates the operation instruction unit to perform a start of an operation, and the control unit performs a first control that lights the ultraviolet light source and a second control that starts the blowing operation of the blower after executing the first control when the control unit receives the treatment start signal transmitted from the operation instruction unit.

5. The gas treatment device according to claim 4, wherein the operation instruction unit transmits a treatment stop signal to the control unit when the operator operates the operation instruction unit to perform a stop of an operation during the lighting of the ultraviolet light source, and the control unit performs a third control that turns off the ultraviolet light source and a fourth control that stops the blowing operation of the blower after executing the third control when the control unit receives the treatment stop signal transmitted from the operation instruction unit.

6. The gas treatment device according to claim 5, wherein the ultraviolet light source is an excimer lamp that radiates ultraviolet light having a main emission wavelength of 172 nm.

7. The gas treatment device according to claim 4, wherein the ultraviolet light source is an excimer lamp that radiates ultraviolet light having a main emission wavelength of 172 nm.

8. The gas treatment device according to claim 3, wherein the ultraviolet light source is an excimer lamp that radiates ultraviolet light having a main emission wavelength of 172 nm.

9. The gas treatment device according to claim 2, wherein the ultraviolet light source is an excimer lamp that radiates ultraviolet light having a main emission wavelength of 172 nm.

10. The gas treatment device according to claim 1, wherein the control unit controls the lighting of the ultraviolet light source.

11. The gas treatment device according to claim 10, further comprising an operation instruction unit that is configured to be operational to an operator, wherein the operation instruction unit transmits a treatment start signal to the control unit when the operator operates the operation instruction unit to perform a start of an operation, and the control unit performs a first control that lights the ultraviolet light source and a second control that starts the blowing operation of the blower after executing the first control when the control unit receives the treatment start signal transmitted from the operation instruction unit.

12. The gas treatment device according to claim 11, wherein the operation instruction unit transmits a treatment stop signal to the control unit when the operator operates the operation instruction unit to perform a stop of the operation during the lighting of the ultraviolet light source, and the control unit performs a third control that turns off the ultraviolet light source and a fourth control that stops the blowing operation of the blower after executing the third control when the control unit receives the treatment stop signal transmitted from the operation instruction unit.

13. The gas treatment device according to claim 12, wherein the ultraviolet light source is an excimer lamp that radiates ultraviolet light having a main emission wavelength of 172 nm.

14. The gas treatment device according to claim 11, wherein the ultraviolet light source is an excimer lamp that radiates ultraviolet light having a main emission wavelength of 172 nm.

15. The gas treatment device according to claim 10, wherein the ultraviolet light source is an excimer lamp that radiates ultraviolet light having a main emission wavelength of 172 nm.

16. The gas treatment device according to claim 1, wherein the ultraviolet light source is an excimer lamp that radiates ultraviolet light having a main emission wavelength of 172 nm.

17. A gas treatment method is a method of treating a gas to be treated, including oxygen, that is introduced at a gas inlet, allowing the gas to be treated to flow through a filter that adsorbs at least ozone, and exhausting a treated gas at a gas outlet disposed at a location different from that of the gas inlet, the gas treatment method comprising:

a step (A) of starting radiation of ultraviolet light from an ultraviolet light source; and a step (B) of starting a blowing operation of a blower to allow the gas to be treated to flow from the gas inlet toward the gas outlet, after executing the step (A).

18. The gas treatment method according to claim 17, further comprising a step (C) of stopping the radiation of the ultraviolet light from the ultraviolet light source, and a step (D) of stopping the blowing operation of the blower, the blowing operation allowing the gas to be treated to flow in the gas channel from the gas inlet toward the gas outlet after executing the step (C).

* * * * *